United States Patent [19]

Bitsch

[11] Patent Number: 4,690,902

[45] Date of Patent: Sep. 1, 1987

[54] METHOD, REAGENT AND KIT FOR THE DETERMINATION OF NITRATE IONS

[75] Inventor: Roland Bitsch, Pfungstadt, Fed. Rep. of Germany

[73] Assignee: Merck Patent Gesellschaft mit beschränkter Haftung, Darmstadt, Fed. Rep. of Germany

[21] Appl. No.: 702,154

[22] Filed: Feb. 15, 1985

[30] Foreign Application Priority Data

Feb. 18, 1984 [DE] Fed. Rep. of Germany ....... 3405912

[51] Int. Cl.⁴ ............................................. G01N 31/22
[52] U.S. Cl. ........................................ 436/110; 422/61
[58] Field of Search ........................ 436/110, 114, 182; 422/61; 562/508, 493, 477, 475; 568/763; 560/105, 8, 103, 109

[56] References Cited

U.S. PATENT DOCUMENTS

| | | | |
|---|---|---|---|
| 2,603,662 | 7/1952 | Stevens | 562/477 X |
| 3,468,942 | 9/1969 | Blum | 562/477 X |
| 3,530,174 | 9/1970 | Gottesman et al. | 562/477 X |
| 3,966,411 | 6/1976 | Ross et al. | 436/110 X |
| 4,003,706 | 1/1977 | Szekely | 436/110 |
| 4,137,258 | 1/1979 | Moore et al. | 562/477 |
| 4,184,923 | 1/1980 | Schubert | 435/25 X |
| 4,357,144 | 11/1982 | Gindler et al. | 422/61 X |
| 4,424,277 | 1/1984 | Bodart | 436/110 |
| 4,474,888 | 10/1984 | Gindler et al. | 422/61 X |

FOREIGN PATENT DOCUMENTS 735982 5/1980 U.S.S.R. ............................... 436/110

OTHER PUBLICATIONS

Lange, et al., Photometrische Analyse, Verlag Chemie Weinheim, 7th Ed., (1980), pp. 365-367.
Grant, "Hackh's Chemical Dictionary", McGraw-Hill Book Co., 1969.

Primary Examiner—David L. Lacey
Assistant Examiner—Jill Johnston
Attorney, Agent, or Firm—Millen & White

[57] ABSTRACT

A method for the colorimetric determination of nitrate ions comprises mixing the sample which is to be investigated with concentrated sulfuric acid and a color-generating compound of the formula

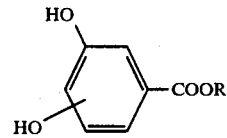

wherein R is H, one equivalent of a cation, or $C_{1-6}$ alkyl. A reagent and kit for colorimetric nitrate determination are also described.

15 Claims, No Drawings

METHOD, REAGENT AND KIT FOR THE DETERMINATION OF NITRATE IONS

BACKGROUND OF THE INVENTION

This invention relates to a method, reagent and kit for the colorimetric determination of nitrate ions in aqueous solutions.

The quantitative determination of nitrate ions is becoming of increasing importance in analysis. Nitrate content in drinking water and service water, in foodstuffs, in agricultural chemistry and in general environmental analysis is increasingly becoming a general criterion of quality. Reliable and economic determination procedures are required for monitoring the amounts of nitrate present in drinking water and the fertilizer residues in foodstuffs, and for determination of the level of nitrate in soils which are used for agriculture, permitting cost-effective mineral fertilizing.

There are relatively few methods for the determination of nitrate ions. The only procedures of importance are of the colorimetric type, and even these are less satisfactory than those for other ions.

There are essentially two different procedures for the determination of nitrate ions, direct nitration and/or oxidation in concentrated sulfuric acid and reduction, with suitable reducing agents, of the nitrate ions to nitrite ions and their determination as an azo dye after the so-called Griess reaction.

Oxidation reactions with anthranilic acid (deep-blue solution), brucine (orange product) or diphenylamine (blue product) have the advantage of a marked reaction contrast, but have the disadvantage of low selectivity, since other ions, for example chloride in sea water, likewise have oxidizing effects under these conditions. Nitration reactions of phenols lead to yellow nitrophenols. In this case, the higher selectivity, even though still hardly adequate for practical purposes, is counteracted by the yellow reaction colors obtained, the differences in intensity of which can be differentiated by eye only with difficulty.

A method for the determination of nitrates using bis-phenols or bis-phenol ethers is described in U.S. Pat. No. 4,424,277.

A method for the determination of nitrates using sodium salicylate is described, in Lange/Vejdelek, *Photometrische Analyse* (Photometric Analysis), Verlag Chemie Weinheim, 7th Edition, 1980, page 365, with the yellow 5-nitrosalicylic acid obtained being determined by photometry. Using that method, it is necessary to remove interfering cations with an ion exchanger, since, for example, nitrates intensify and bromides and iodides reduce the intensity of the color obtained. The determination is very elaborate; the sample containing the reagent must be evaporated to dryness by heating at 100°-120° C. After cooling, 96% sulfuric acid is added to the dried residue. Then, only after the addition of water, alkali solution, making up to the mark in a graduated flask with water and standing for 20 minutes, can the determination be carried out.

In general, the previously known methods are lengthy, require a considerable expenditure in apparatus, and are more or less susceptible to interference or are too sensitive for practical requirements.

OBJECTS OF THE INVENTION

Accordingly, one object of the present invention is to provide a method for the determination of nitrate ions, with which very small nitrate contents can be directly determined in a reliable and reproducible manner and without special pretreatment of the sample.

Another object of the invention is to provide a reagent for the colorimetric determination of nitrate ion.

A further object of the invention is to provide a kit for colorimetric nitrate ion determinations.

Upon further study of the specification and appended claims, further objects and advantages of this invention will become apparent to those skilled in the art.

SUMMARY OF THE INVENTION

These and other objects of the invention are achieved by providing a method for the colorimetric determination of nitrate ions, comprising admixing a sample with concentrated sulfuric acid and a color-generating compound having the formula

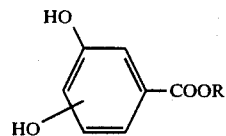

wherein R is H, one equivalent of a cation, or branched or unbranched $C_{1-6}$ alkyl.

In a composition of matter aspect, a color-generating reagent is provided for colorimetric nitrate ion determinations, consisting essentially of a compound having that formula dissolved in sulfuric acid.

A kit for colorimetric nitrate ion determinations comprises the foregoing compound and a container of concentrated sulfuric acid.

DETAILED DISCUSSION

Surprisingly, it has been found that certain benzoic acid derivatives produce with nitrate ions, in the presence of concentric sulfuric acid, color reactions which meet the simultaneous requirements of reaction contrast and simplicity of procedure. In comparison with the known methods, accurate control of the temperature of the measurement mixture is unnecessary for reproducibility of the measurement; the maximum optical density is reached after only a few minutes and is constant for hours; and the manner and duration of mixing the reagents have no effect on the measured values.

Preferred color-generating compounds for practicing the present invention are 3,5- and 2,5-dihydroxybenzoic acid and their salts with alkali metal ions, one equivalent of alkaline earth metal ions or other metal ions which do not give precipitates or colors with sulfuric acid, such as Li, Na, K, Rb, Cs, Mg, Zn and $NH_4$, as well as the corresponding esters of those dihydroxybenzoic acids with alcohols having 1 to 6 C atoms, which alcohols can be straight-chain or branched. Accordingly, examples of the radical R are alkyl such as methyl, ethyl, propyl, iso-propyl, butyl, iso-butyl, pentyl, iso-pentyl, hexyl, and iso-hexyl. 3,5-Dihydroxybenzoic acid is particularly preferred.

Ions interfering with the determination of nitrate ions according to the invention are essentially the following: nitrite, chlorate, bromate, iodate, sulfide and iodide. Nitrite can be eliminated from the sample with sulfamic acid, the other ions by reduction with sulfite in an acidic medium.

The concentration of the color-generating compound can be varied within wide limits. Suitable compound concentrations are in the range from about 0.1 to 1.0% by weight in the measurement mixture, i.e., compound, sulfuric acid and sample, the mixture whose color is to be correlated with a calibrated reference standard. In the case of 3,5-dihydroxybenzoic acid, a suitable concentration in the measurement mixture is about 0.2 to 1.0, preferably about 0.6% by weight. Concentrations of the compound which are too low give colorless blanks, but the red color obtained in the presence of nitrate ions is stable for only a short time. Reproducible nitrate determinations require an excess of compound; but too high a concentration results in a pale brown blank. Also, the upper limit for compound concentration is determined by its solubility.

The color reaction is carried out at a sulfuric acid concentration of about 81 to 86% by weight, preferably about 83 to 84% by weight, in the measurement mixture. An appropriate amount of sample-containing solution is added to the reagent (color-generating compound in concentrated sulfuric acid) to achieve the concentration of sulfuric acid desired. Higher or lower concentrations produce less intense colors. In place of the sulfuric acid, it is also possible to use a mixture of sulfuric acid and phosphoric acid, e.g., up to 5 mole % of the sulfuric acid can be replaced by the phosphoric acid.

For convenience in using, the color-generating compound can be provided as a kit in a container together with concentrated (e.g., 96%) sulfuric acid.

The determination of nitrate ions is carried out in such a manner that the reagent is dissolved in concentrated sulfuric acid, the sample solution which is to be investigated is added, and the solution is mixed. It is also possible to add first the reagent and then the sulfuric acid to the sample solution. The reaction is complete after only a few minutes and it can be evaluated either visually using a color scale or by photometry.

A color gradation from pale brown to deep wine-red, which can be very easily differentiated visually, is obtained when the nitrate ions are present in the sample solution which is to be investigated in a concentration range from about 10 to 100 mg/l. The color of the solution is photometrically stable for at least 4 hours. The concentration range, which is of interest, for example for the analysis of drinking water or water from industrial regions, is between 10 and 200 ppm of nitrate ions in the water. The measurement range can be displaced upwards or downwards by varying the path length of the cell.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

70 mg of 3,5-dihydroxybenzoic acid are dissolved in 5 ml of 96% sulfuric acid. 1.5 ml of sample solution, which can contain between 10 and 100 mg/l nitrate ions, is pipetted into this solution. The mixture heats up to about 90°–100° C. Depending on the content of nitrate ions, a clear color gradation from pale brown to deep red is detectable after 2 to 3 minutes, and this can be assigned, using a scale with graded color values, unambiguously to the appropriate content or nitrate ions. For spectrophotometric evaluation, the reaction is measured in a cell path length 10 mm in a spectrophotometer at 525 nm with a blank sample prepared at the same time as the reference. Using the measured extinction, the concentration of nitrate ions is read off from a calibration curve previously drawn up using solutions containing accurately known amounts of nitrate ions.

EXAMPLE 2

Using the procedure of the prevous example, analogous results are obtained when 2,5-dihydroxybenzoic acid is added in place of 3,5-dihydroxybenzoic acid. In this case, the color gradation runs from pale brown to orange-yellow. For spectrophotometric evaluation, the measurement is carried out at 420 nm. As in the previous example, using the measured extinction, the concentration of nitrate is read off from a calibration curve previously prepared using solutions containing accurately known amounts of nitrate ions.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for the colorimetric determination of nitrate ions comprising admixing a sample with concentrated sulfuric acid and a color-generating compound having the formula

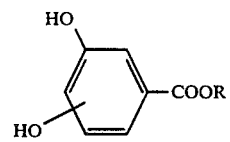

wherein R is H, one equivalent of a cation compatible with nitrate ion determination, or $C_{1-6}$ alkyl, said color-generating compound being present in an amount effective to produce a quantitative coloration obtaining a resultant admixture and correlating the color of the resultant admixture with a calibrated reference standard.

2. A method according to claim 1, wherein the color generating compound is 2,5-dihydroxybenzoic acid.

3. A method according to claim 1, wherein the resultant admixture contains about 83–84% by weight of sulfuric acid.

4. A method according to claim 1, wherein the sample is in the form of a solution containing about 10 to 100 mg/l nitrate ions.

5. A method according to claim 1 wherein the resultant admixture contains 81–86% by weight of sulfuric acid.

6. A method according to claim 5, wherein the resultant admixture contains about 0.6% by weight of the color-generating compound.

7. A method according to claim 5, wherein the resultant admixture contains about 0.1 to 1.0% by weight of the color-generating compound.

8. A method according to claim 1 wherein the color generating compound is 3,5-dihydroxybenzoic acid.

9. A method according to claim 8, wherein the resultant admixture contains about 0.2 to 1.0% by weight of 3,5-dihydroxybenzoic acid.

10. A method according to claim 9, wherein the resultant admixture contains 81–86% by weight of sulfuric acid.

11. A method according to claim 9, wherein the resultant admixture contains about 83–84% by weight of sulfuric acid.

12. A reagent for colorimetric nitrate ion determination, consisting essentially of a solution of a compound having the formula

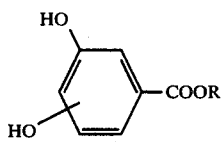

wherein R is H, one equivalent of a cation compatible with nitrate ion determination or $C_{1-6}$ alkyl, and concentrates sulfuric acid, said compound and said concentrated sulfuric acid being present in amounts effective to produce a quantitative coloration.

13. A reagent according to claim 12, wherein the compound is 3,5-dihydroxybenzoic acid.

14. A reagent according to claim 12, wherein the compound is 2,5-dihydroxybenzoic acid.

15. A kit for colorimetric nitrate ion determination, comprising a container of a compound having the formula

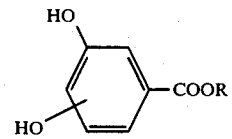

wherein R is H, one equivalent of a cation compatible with nitrate ion determination or $C_{1-6}$ alkyl, and a container of concentrated sulfuric acid.

* * * * *